United States Patent
Bhatt et al.

(10) Patent No.: US 6,946,055 B2
(45) Date of Patent: Sep. 20, 2005

(54) METHOD FOR RECOVERING AN ORGANIC SOLVENT FROM A WASTE STREAM CONTAINING SUPERCRITICAL $CO_2$

(75) Inventors: Anilkumar C. Bhatt, Johnson City, NY (US); Jerome J. Wagner, Endicott, NY (US)

(73) Assignee: International Business Machines Corporation, Armonk, NY (US)

( * ) Notice: Subject to any disclaimer, the term of this patent is extended or adjusted under 35 U.S.C. 154(b) by 714 days.

(21) Appl. No.: 09/934,864

(22) Filed: Aug. 22, 2001

(65) Prior Publication Data

US 2003/0044340 A1 Mar. 6, 2003

(51) Int. Cl.[7] .............................. B01D 1/00; B01D 3/14; C01B 3/20; C01B 3/24; C23F 1/46
(52) U.S. Cl. .............................. 159/47.3; 159/DIG. 16; 203/73; 203/80; 216/93; 423/220; 423/419.1; 558/260
(58) Field of Search ................... 159/47.3, DIG. 16; 203/73, 80; 216/93; 558/260; 423/419.1, 220; 210/768, 800, 806; 118/61

(56) References Cited

U.S. PATENT DOCUMENTS

| | | | |
|---|---|---|---|
| 4,877,530 A | * 10/1989 | Moses | 210/511 |
| 5,281,723 A | 1/1994 | Bantu et al. | 549/230 |
| 5,377,705 A | * 1/1995 | Smith et al. | 134/95.3 |
| 5,843,311 A | 12/1998 | Richter et al. | 210/634 |
| 5,868,856 A | 2/1999 | Douglas et al. | 134/2 |
| 5,868,862 A | 2/1999 | Douglas et al. | 134/26 |
| 5,908,510 A | 6/1999 | McCullough et al. | 134/2 |
| 5,965,465 A | 10/1999 | Rath et al. | 438/745 |
| 6,001,216 A | 12/1999 | Lee | 156/345 |
| 6,005,764 A | 12/1999 | Anderson et al. | 361/500 |
| 6,033,996 A | 3/2000 | Rath et al. | 438/756 |
| 6,063,899 A | 5/2000 | Johnson et al. | 528/482 |
| 6,146,533 A | * 11/2000 | Nakai et al. | 210/634 |
| 6,187,965 B1 | * 2/2001 | Bhatt et al. | 568/810 |
| 6,306,564 B1 | * 10/2001 | Mullee | 430/329 |
| 6,423,290 B1 | * 7/2002 | Bhatt et al. | 423/488 |
| 6,506,259 B1 | * 1/2003 | Romack et al. | 134/10 |
| 6,764,552 B1 | * 7/2004 | Joyce et al. | 134/3 |

FOREIGN PATENT DOCUMENTS

| | | |
|---|---|---|
| JP | 07-070080 A | 3/1995 |
| JP | 11-513042 A | 11/1999 |
| JP | 11-335372 A | 12/1999 |
| JP | 2001-194807 A | 7/2001 |
| WO | WO-01/33613 A2 | 5/2001 |

* cited by examiner

*Primary Examiner*—Virginia Manoharan
(74) *Attorney, Agent, or Firm*—Connolly, Bove, Lodge & Hutz, LLP; Arthur J. Samodovitz

(57) ABSTRACT

An organic solvent is separated from a waste stream containing supercritical $CO_2$, an organic solvent and etchant contaminants. The process includes separating the supercritical $CO_2$ by subjecting the waste stream to elevated temperature and/or reduced pressure to thereby obtain a first composition containing the supercritical $CO_2$ and a second composition containing the organic solvent and being substantially free of the supercritical $CO_2$; and then removing non-volatile etching contaminants from the second stream search as by at least one of the following:

evaporation;
distillation;
filtration;
centrifugation;
and settling.

20 Claims, 1 Drawing Sheet

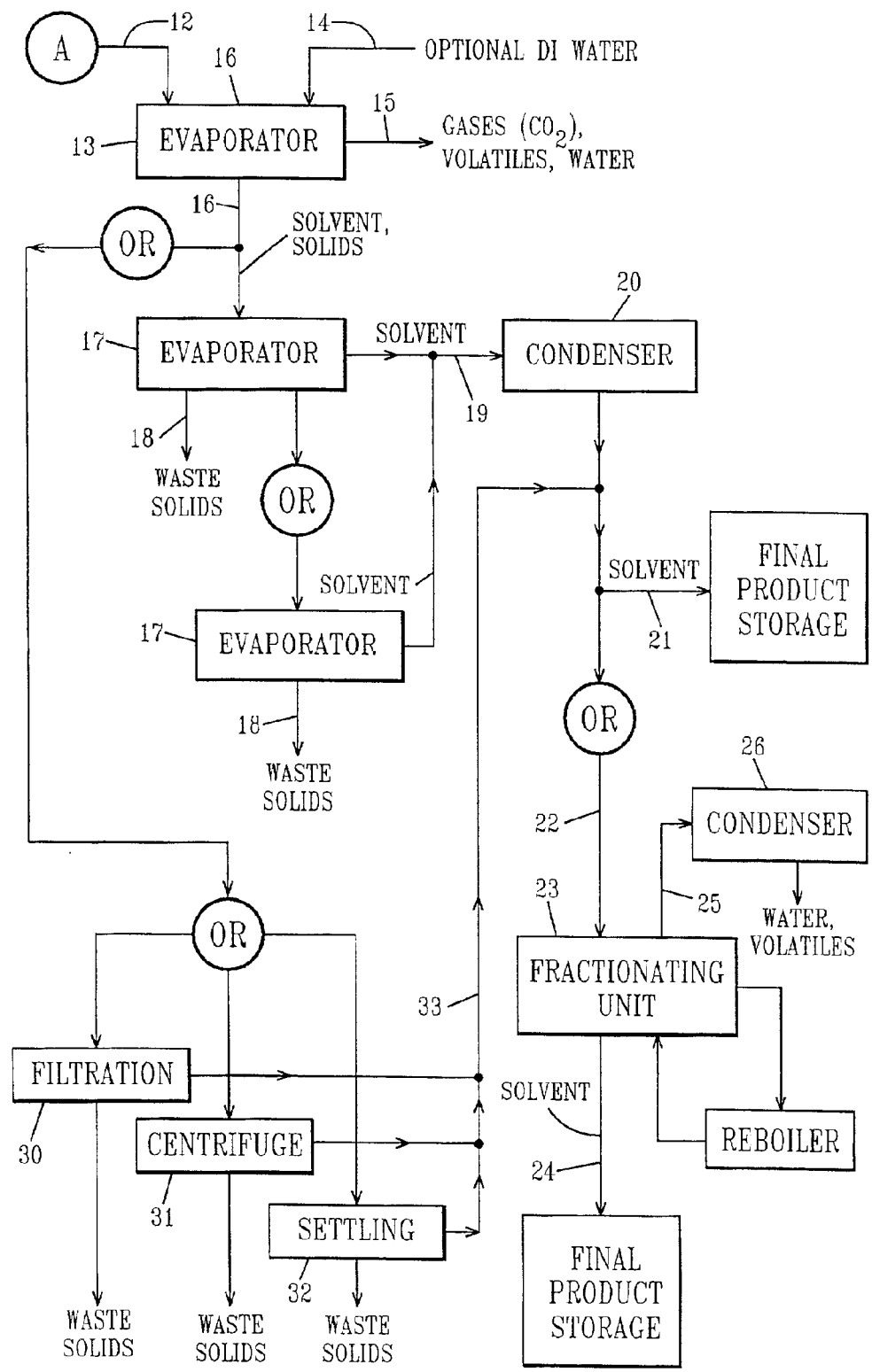

METHOD FOR RECOVERING AN ORGANIC SOLVENT FROM A WASTE STREAM CONTAINING SUPERCRITICAL CO₂

FIELD OF THE INVENTION

The present invention relates to a method for recovering an organic solvent from a waste stream containing the organic solvent, supercritical carbon dioxide ($CO_2$) and other contaminants. The method of the present invention is especially useful for treating waste streams that contain supercritical $CO_2$ and the organic solvent along with contaminants from etching in fabricating integrated circuit products. The organic solvent of especial interest according to the present invention is propylene carbonate.

BACKGROUND OF INVENTION

In the fabrication of microelectronic components, a number of the steps involved, for instance, in preparing integrated circuit chips and the packaging for the chips (articles to which the chips are attached and protected) are etching processes. Accordingly, over the years, a number of vastly different types of etching processes to remove material, sometimes in selective areas, have been developed and are utilized in varying degrees. Moreover, the steps of etching different layers which constitute, for instance, the finished integrated circuit chip, are among the most critical and crucial steps.

One method widely employed for etching is to overlay the surface to be etched with a suitable mask and then immerse the surface and mask in a chemical solution which attacks the surface to be etched, while leaving the mask intact and while only etching other materials of the article to at most, a minimum extent.

Recently, selective etch processes employing etching compositions comprising supercritical $CO_2$ and an organic solvent, preferably propylene carbonate, have been developed and suggested for etching various materials. Use of these compositions has provided improved properties such as a wider process window as well as enhanced selective performance.

However, use of these etching compositions results in waste streams containing the supercritical $CO_2$, organic solvent, and a wide variety of etchant contaminants such as silicon dioxide, silicon nitride, ammonium fluoride ($NH_4F$) and the like.

It would therefore be desirable to provide a method for treating the waste stream at least from both economic and environmental viewpoints. Moreover, proper recovery of the solvent would yield for reuse, a superior etchant as regards process control and function.

SUMMARY OF INVENTION

The present invention relates to a method for treating a waste stream that contains both supercritical $CO_2$ and an organic solvent to remove the supercritical $CO_2$ and recovery the organic solvent. In particular, the present invention provides a method that is reasonable from an economic viewpoint for recouping and repurifying the organic solvent in the contaminated waste stream. Accordingly, the present invention is beneficial from an ecological viewpoint along with reducing or avoiding waste disposal, reducing waste disposal costs, and reducing raw materials purchase costs.

In particular, the method of the present invention relates to treating a waste stream that comprises supercritical $CO_2$, an organic solvent and non-volatile etchant contaminants by separating the supercritical $CO_2$ from the waste stream to thereby obtain a first composition containing the supercritical $CO_2$ and a second stream containing the organic solvent and being free of the supercritical $CO_2$. The separation can be carried out subjecting the waste stream to elevated temperatures and/or reduced pressure.

Next the etching contaminants are removed from the second stream containing the organic solvent to recover the organic solvent free of the etching contaminants. Typical processes that can be used for this purpose are evaporation, distillation, filtration, centrifugation and settling.

Still other objects and advantages of the present invention will become readily apparent by those skilled in the art from the following description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

SUMMARY OF DRAWINGS

The FIGURE is a flow diagram illustrating various alternative procedures for separating the supercritical $CO_2$ from the waste stream and organic solvent.

BEST AND VARIOUS MODES FOR CARRYING OUT INVENTION

The etching compositions which are used and subsequently result in the waste streams treated according to the present invention comprise supercritical $CO_2$ and an organic solvent. The organic solvent employed includes oxolanes, sulfoxolanes, esters, ketones, aldehydes, lactones, halogenated solvents, amines, imides and monohydric alcohols. Examples of suitable esters are esters of carboxylic acids, benzoic acid, phthalic acid, isophthalic acid and terephthalic acid, and especially the $C_1$–$C_6$ alkyl esters. Preferred organic solvents are propylene carbonate, homologs of propylene carbonate, N-methyl pyrrolidone, gamma butyrolactone, methylene chloride, benzyl alcohol, N-formyl morpholine, N-formyl piperidine, cyclohexanone, cyclopentanone, methyl benzoate, diglyme, 2-methyl tetrahydrofuran, and methyl and ethyl esters of phthalic, isophthalic or terephthalic acids. The more preferred solvents employed are propylene carbonate, N-methyl pyrrolidone and gamma butyrolactone, with propylene carbonate, and homologs thereof being the most preferred.

Examples of homologs of propylene carbonate can be represented by the formula:

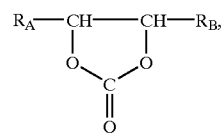

where $R_A$ and $R_B$ are short chain alkyl groups or hydrogen. Exemplary short chain alkyl groups are $CH_3$—$(CH_2)_n$—, where n in $R_A$ and $R_B$ are independent integers from 0 to 3.

The compositions typically contain about 0.1 to about 3 molar of the supercritical $CO_2$ and the remainder being the organic solvent.

These etching compositions, depending upon various modifications such as are used to etch various materials such as silicon nitride, various silicon dioxides, and ammonium fluoride inter alia.

Accordingly, the waste stream from the etching process contains supercritical $CO_2$, and the organic solvent, preferably propylene carbonate, along with etchant contaminants such as silicon dioxide, silicon nitride, and/or ammonium fluoride. In addition, in the event water was present in the etchant composition, or otherwise became incorporated during etchant use, such will likewise be present in the waste stream.

Reference to the FIGURE illustrates an embodiment of the present invention along with various alternatives suitable for carrying out the process of the present invention. In particular, the FIGURE illustrates conveying the waste via conduit 12 to a preheater or evaporator 13. If desired as an optional step, deionized water can be added to the evaporator 13 via conduit 14 to help reduce the loss of solvent there. The evaporator 13 is run at temperatures, times and pressures sufficient to expel the $CO_2$ (such as under vacuum).

The temperature and pressure conditions required to remove the $CO_2$ depend on the identity of the particular solvent being used and the degree of removal which must be achieved. Typically, temperatures are about 20° C. to about 150° C.; pressures are about 15 torr to about 760 torr. When the solvent is propylene carbonate, temperatures are typically about 20° C. to about 130° C. and pressures are about 15 torr to about 75 torr. In the preferred embodiment, which uses propylene carbonate, the most preferred temperature is 120° C. and, the most preferred pressure is about 25 torr. The residence time of the waste at these conditions would vary with the removal requirements; which typically is about one second to about one hour. In the next preferred embodiment, residence time in the evaporator is about 10 seconds. The $CO_2$, and other volatiles, and water are removed via conduit 15 and the organic solvent along with any waste solids that might be carried with it is removed via conduit 16.

The stream via conduit 16 can be fed to an evaporator, especially a wiped film evaporator (WFE) 17 to separate remaining waste solids from the organic solvent. The waste solids are removed at exit 18 and the organic solvent is removed at conduit 19.

If desired, a plurality of evaporators 17 as shown in the FIGURE can be employed to help improve solvent yield.

Solvent from the evaporators can be conveyed such as via conduit 19 to a condenser 20.

In the alternative or in addition thereto, the stream can be conveyed to a filtration means 30 or centrifuge process 31 or settling process 32 to separate waste solids from the organic solvent. Other means might also be applied. The particular parameters for these processes can be determined by persons skilled in the art and aware of this disclosure. For instance, for a filtration process, such design factors as sequential filtration, pore size, surface area, and materials of construction are considered by the user to optimize operating factors (such as flow rate, pressure drop, and service life) with desired product quality. For a centrifuge process, factors such as rotational speed and residence time are considered relative to etchant media characteristics. For a setting process, factors such as residence time, superficial velocity, and available space are considered.

The solvent from any of these processes can then be conveyed such as via conduit 33 to storage via conduit 21. In the alternative, the solvent can be conveyed via conduit 22 to a fractionation unit 23 to undergo fractional distillation. This results in an organic solvent fraction being removed via exit 24 and sent to storage and water and other low boiling volatiles and gases being removed at exit 25 and sent to condenser 26.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A method for recovering an organic solvent from a waste stream comprising supercritical $CO_2$ an organic solvent and etching contaminants which comprises:
    a) separating the supercritical $CO_2$ by subjecting the waste stream to elevated temperature or reduced pressure or both, to thereby obtain a first composition containing the supercritical $CO_2$ and a second composition containing the organic solvent and being at least substantially free of the supercritical $CO_2$, and then
    b) removing non-volatile etching contaminants from the second composition to recover the organic solvent free of the etching contaminants
    wherein said temperature is about 20° C. to about 150° C. and said pressure is about 15 to about 760 torr, and wherein the step of separating is by evaporation.

2. The method of claim 1 which comprises removing the non-volatile etching contaminants via evaporation.

3. The method of claim 2 wherein the evaporation comprises sequential evaporations.

4. The method of claim 1 which comprises removing the non-volatile etching contaminants by distillation.

5. The method of claim 4 wherein the distillation comprises fractional distillation.

6. The method of claim 1 which comprises removing the non-volatile etching contaminants by filtration.

7. The method of claim 1 which comprises removing the non-volatile etching contaminants by centrifugation.

8. The method of claim 1 which comprises removing the non-volatile etching contaminants by settling.

9. The method of claim 1 wherein the organic solvent is selected from the group consisting of propylene carbonate, homologs thereof, N-methyl pyrrolidone and gamma butyrolactone.

10. The method of claim 1 wherein the organic solvent comprises propylene carbonate or homolog thereof.

11. The method of claim 1 wherein the organic solvent comprises propylene carbonates.

12. The method of claim 1 wherein the waste stream contains about 0.1 to about 3 molar of the supercritical $CO_2$.

13. The method of claim 1 wherein the etching contaminants comprises at least one member selected from the group consisting of silicon nitride, silicon dioxide, and ammonium fluoride.

14. A method for recovering propylene carbonate from a waste stream comprising supercritical $CO_2$, propylene carbonate and etching contaminants which comprises:
    a) separating the supercritical $CO_2$ by subjecting the waste stream to elevated temperature or reduced pressure or both, to thereby obtain a first composition containing the supercritical $CO_2$ and a second composition containing propylene carbonate and being at least substantially free of the supercritical $CO_2$, and then b) removing non-volatile etching contaminants from the second composition by at least one process selected from the group consisting of evaporation, distillation, filtration, centrifugation and settling to recover the organic solvent free of the etching contaminants and wherein said temperature is about 20° C. to about 130° C. and said pressure is about 15 to about 75 torr.

15. The method of claim 14 wherein the waste stream contains about 0.1 to about 3 molar of the supercritical $CO_2$.

16. The method of claim 15 wherein the etching contaminants comprises at least one member selected from the group consisting of silicon nitride, silicon dioxide, and ammonium fluoride.

17. The method of claim 14 wherein the etching contaminants comprises at least one member selected from the group consisting of silicon nitride, silicon dioxide, and ammonium fluoride.

18. The method of claim 14 which comprises removing the non-volatile etching contaminants via evaporation.

19. The method of claim 14 which comprises removing the non-volatile etching contaminants by distillation.

20. The method of claim 14 which comprises removing the non-volatile etching contaminants by centrifugation.

* * * * *